United States Patent
Eriksson

(12) 
(10) Patent No.: US 6,683,302 B1
(45) Date of Patent: Jan. 27, 2004

(54) METHOD AND DEVICE FOR ELECTROSPRAY IONIZATION

(75) Inventor: Johan Eriksson, Uppsala (SE)

(73) Assignee: Amersham Biosciences AB, Uppsala (SE)

(*) Notice: Subject to any disclaimer, the term of this patent is extended or adjusted under 35 U.S.C. 154(b) by 0 days.

(21) Appl. No.: 10/148,717

(22) PCT Filed: Nov. 28, 2000

(86) PCT No.: PCT/EP00/11859

§ 371 (c)(1),
(2), (4) Date: Aug. 28, 2002

(87) PCT Pub. No.: WO01/40791

PCT Pub. Date: Jun. 7, 2001

(30) Foreign Application Priority Data

Nov. 29, 1999 (SE) ............................... 9904318

(51) Int. Cl.[7] .......................... H01J 49/00; B01D 59/44
(52) U.S. Cl. ........................ 250/288; 250/281; 250/282
(58) Field of Search ........................... 250/281, 282, 250/288

(56) References Cited

U.S. PATENT DOCUMENTS

| 4,546,253 A | * | 10/1985 | Tsuchiya et al. | ............ 250/288 |
|---|---|---|---|---|
| 4,842,701 A | * | 6/1989 | Smith et al. | ................ 204/451 |
| 4,935,624 A | | 6/1990 | Henion et al. | |
| 5,481,107 A | * | 1/1996 | Takada et al. | ............. 250/288 |
| 6,586,731 B1 | * | 7/2003 | Jolliffe | ....................... 250/288 |

OTHER PUBLICATIONS

Mehdi, M., et al. "Atmospheric Pressure Microwave Induced Plasma Ionization Source for Molecular Mass Spectrometry" Journal of the American Society for Mass Spectrometry, Elsevier Science Inc., US. vol. 9, No. 1, 1998, pp. 42–79.

* cited by examiner

*Primary Examiner*—John R. Lee
*Assistant Examiner*—Paul M. Gunzo
(74) *Attorney, Agent, or Firm*—Royal N. Ronning, Jr.; Stephen G. Ryan

(57) ABSTRACT

The present invention relates to electrospray device and a method for heating a liquid in said electrospray device. The device comprising a liquid source (3), a mass analyser (5), and inlet plate (17) with an inlet orifice (19), liquid inlet means such as a capillary tube (9) having a spray tip (11) for emitting liquid from said liquid source (3) and it further comprises microwave energy emitting means (21) between said spray tip (11) and said mass analyser (5) for heating said liquid.

7 Claims, 2 Drawing Sheets

METHOD AND DEVICE FOR ELECTROSPRAY IONIZATION

FIELD OF THE INVENTION

The present invention relates to devices and methods for assisting ionisation of liquid samples for subsequent mass spectrometer analysis.

PRIOR ART

Mass spectrometers are often used to analyse the masses of components of liquid samples obtained from analysis devices such as liquid chromatographs. Mass spectrometers require that the component sample that is to be analysed be provided in the form of free ions and it is usually necessary to evaporate the liquid samples in order to produce a vapour of ions. This is commonly achieved by using electrospray ionisation. In electrospray ionisation (ESI) a spray is generated by applying a voltage (in the order of 2–3 kV) to a hollow needle through which the liquid sample can freely flow. The inlet orifice to the mass spectrometer is given a lower potential, for example 0V, and an electrical field is generated from the tip of the needle to the orifice of the mass spectrometer. The electrical field attracts the positively charge species in the fluid which accumulate in the meniscus of the liquid at the tip of the needle. The negatively charged species in the fluid are neutralised. This meniscus extends towards the oppositely charged orifice and forms a "Taylor cone". When the attraction between the charged species and the orifice exceeds the surface tension of the tip of the Taylor cone, droplets break free from the Taylor cone and fly in the direction of the electrical field lines towards the orifice. During the flight towards the orifice the liquid in the droplets evaporates and the net positive charge in the droplet increases. As the net charge increases, the columbic repulsion between the like charges in the droplet also increases. When the repulsion force between these like charges exceeds the liquid surface tension in the droplet, the droplet bursts into several smaller droplets. The liquid in these droplets in turn evaporates and these droplets also burst. This occurs several times during the flight towards the orifice.

There are two theories about how the analytes in the liquid enter the vapour phase as free ions. In the first theory, known a the ion desorption method, it is assumed that when the droplet size reduces to a certain small volume, the repulsion between the charged molecules in the droplet will cause the molecules to penetrate the liquid surface and enter the vapour phase. As the droplets continue to shrink, more and more molecules enter the vapour phase.

In the second theory, known as the charged residue mechanism, it is assumed that there comes a stage where each droplet is very small and each one only contains one analyte molecule. As the last molecules of solvent, usually water, evaporate from the droplet, the excess of positive charges in the water is transferred to the analyte molecule which is now in the vapour phase. For the purposes of the invention, it does not matter which theory is correct. A problem with electrospray ionisation is that at high flow rates (e.g. over about 10 microliters per minutes) the average size of the droplets increases. Many of these droplets hit the inlet plate and are neutralised before the molecules of interest have entered the vapour phase. This means that these molecules will not be analysed which leads to reduced sensitivity.

U.S. Pat. No. 4,935,624 teaches an improved method and apparatus for forming ions at atmospheric pressure from a liquid and for introducing the ions into a mass analyser. It attempts to overcome the disadvantage of electrospray ionisation when used for flows much greater than 10 microliters per minute e.g. up to about 2000 microliters per minute. In this document, the apparatus for forming ions comprises a capillary tube that receives the liquid from a liquid chromatograph, and a thermal energy means for directly or indirectly heating the liquid in the capillary tube. The thermal energy means could be provided by electrically resistive heating, piezoelectric heating, ultrasonic heating, infrared heating, microwave heating and conduction from gas heating. The addition of extra heat disperses the droplets into a fine mist. This device suffers from the disadvantage that the heating of the liquid takes place in a capillary tube which means that heating of the droplets is not homogeneous—as the capillary wall inevitably is warm some of the heating takes place from the outside of the droplet towards the inside of the droplet due to the contact between the droplet and the warm capillary wall. Therefore some of the liquid may boil while the rest of the liquid is barely warmed. This is disadvantageous because if the liquid boils then the electrochemical reaction that generates the excess of positive charges which promotes the spray will not occur, while if the liquid is barely heated then the droplets will not evaporate quickly enough on their flights to the orifice.

SUMMARY OF THE INVENTION

The purpose of the present invention is to provide devices and methods which overcome the disadvantages of the prior art devices and methods for assisting the ionisation of liquid samples for subsequent mass spectrometer analysis. This is achieved by means of a device having the characterising features of claim 1 and a method having the characterising features of claim 4.

In particular, in a first embodiment of a device in accordance with the present invention, a microwave-emitting device is positioned between the spray tip of a tube that receives the liquid from a source such as a liquid chromatograph and the target orifice. In this way the droplets are heated in a homogeneous way by the microwaves emitted from the microwave-emitting device.

DETAILED DESCRIPTION OF EMBODIMENTS ILLUSTRATING THE INVENTION

Figure 1:
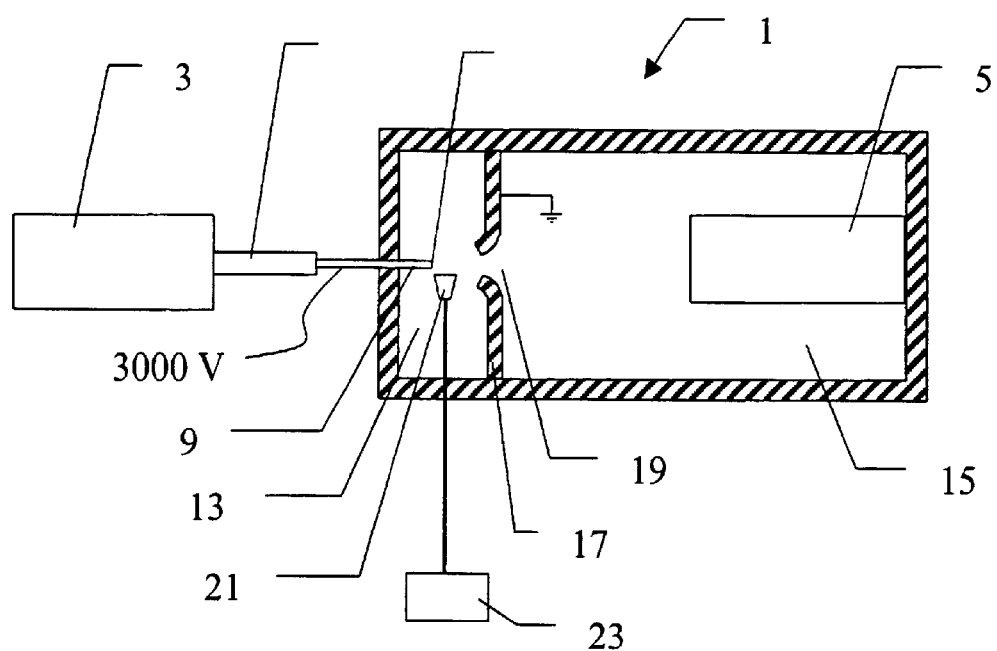
FIG. 1 shows a diagrammatic view of a first embodiment of a device in accordance with the present invention; and, FIG. 2 shows diagrammatically different possible positions for a microwave-emitting means in accordance with the invention.

FIG. 1 shows diagrammatically an electrospray device 1 in accordance with the invention in which practical details which are not related to the present invention are omitted form the sake of ease and clarity of illustration. In the electrospray device 1, liquid that contain molecules to be analysed, and issuing from a liquid source, for example a liquid chromatograph 3, is analysed by a mass analyser such as a mass spectrometer 5. The liquid is led from the liquid chromatograph 3 through an outlet tube 7 that leads to a discharge tube 9 for the mass spectrometer 5. This discharge tube 9 is typically in the form of a capillary tube 9 which has an spray tip 11 which projects into the ionisation chamber 13 of the device 1. The capillary tube 9 is connected to an electrical potential of, for example, 3000 Volts. The ionisation chamber 13 is separated from the mass spectrometer vacuum chamber 15 by an inlet plate 17 containing an inlet orifice 19 at a lower potential, for example, earth potential. Electrically charged liquid drops leave the spray tip 11 of capillary tube 9 and evaporate as they travel towards the inlet orifice 19. This leads to ionisation of the sample molecules in the liquid. A microwave emitting means, such as a microwave head 21, is positioned in the ionisation chamber 13 close to the spray tip 11 of said capillary tube 9. The microwave head 21 is aligned towards the liquid issuing from said spray tip 11 of said capillary tube 9. The microwave head 21 can be controlled by control means 23 to emit microwaves of the appropriate frequency and power needed to heat up the liquid issuing from the spray tip 11 of the capillary tube 9 so that the liquid evaporates more rapidly. In the event that the liquid is an aqueous solution then microwaves having a frequency of 2.45 GHz may be used. Other liquids that have a high dipole moment will also increase their thermal energy when exposed to microwave radiation. As the microwave energy penetrates the liquid, it heats up the liquid homogeneously, thereby avoiding that some of the liquid boils while some of the liquid remains cold.

Figure 2:
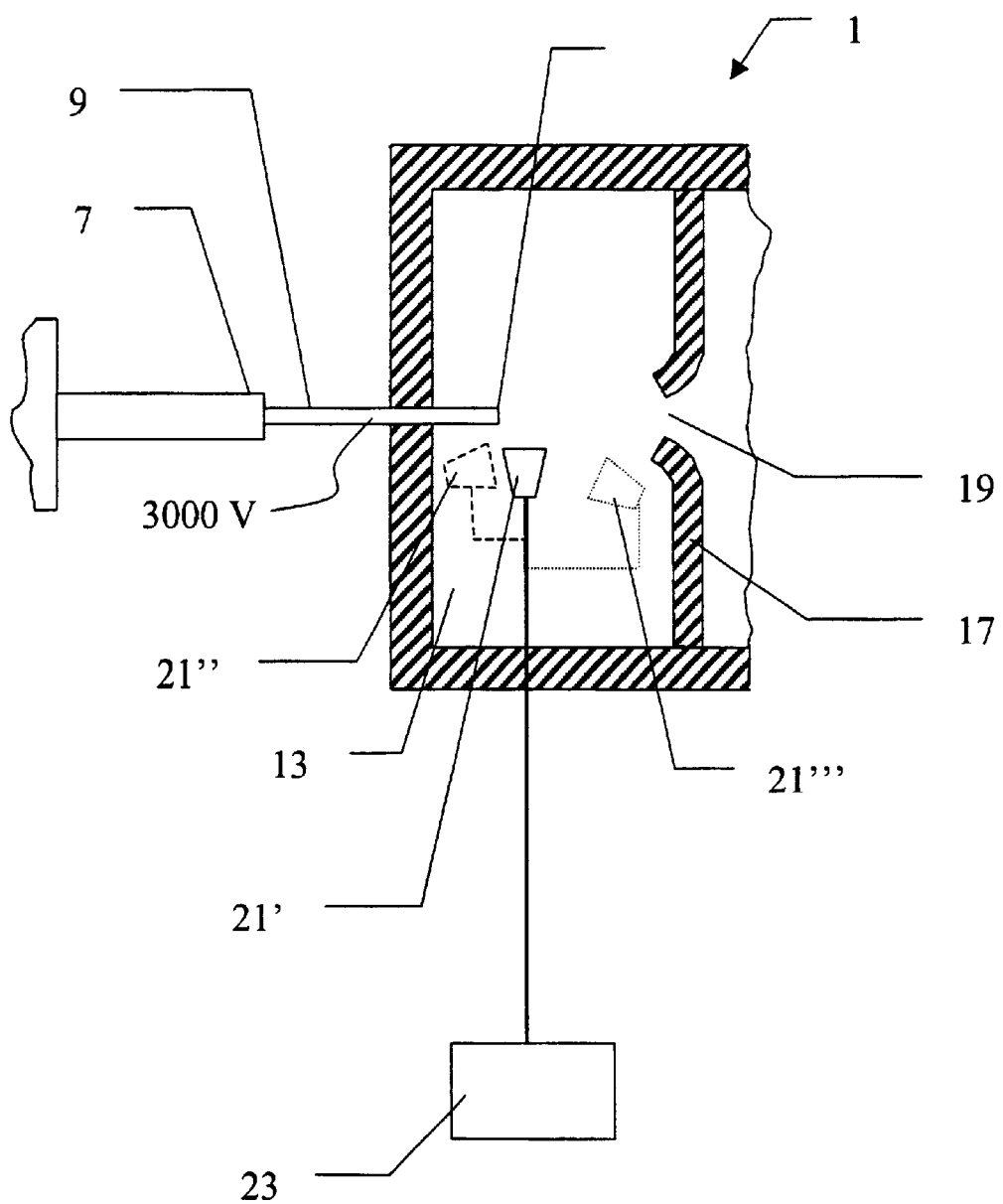

FIG. 2 shows diagrammatically a number of different possible positions for a microwave-emitting means. In a first position, shown in solid lines the microwave-emitting means 21' is positioned in front of, and to one side of, the spray tip 11 of the capillary tube. In this position it directs microwave energy to the droplets at an angle which substantially perpendicular to the line of flight of the liquid droplets. This means that each droplet can only be exposed to microwave radiation when it passes directly in front of the microwave-emitting means. In a second position, shown by dashed lines, the microwave-emitting means 21" is positioned behind the spray tip 11 of the capillary tube 9 and points in the direction towards the orifice. This means that droplets can be almost continuously exposed to microwave energy as they fly towards the orifice. The intensity of the microwave energy and the size of the droplets decrease as the droplets approach the orifice. This ensures that the droplets are heated for a sufficiently long time to cause the fluid to evaporate while at the same time the risk of boiling the progressively smaller droplets is reduced. In a third position, shown by dotted lines, a microwave-emitting means 21''' is positioned near to the inlet plate 17 and faces back towards the capillary tube 9. In this position, the intensity of the microwave energy that can be received by droplets increases as the droplets approach the inlet plate 17 and orifice 19. This ensures that all droplets evaporate before they reach the inlet plate 17. It is of course conceivable to use a plurality of microwave-emitting means 21–21''' placed in any or all of the above mentioned positions or even other positions in order to obtain the advantages provided by the various positions. It is also possible to arrange that micro-wave energy is emitted in a continuous mode or in a pulsed mode or as a pulsed mode superimposed on a continuous mode.

When the microwave-emitting means is positioned in the vicinity of the capillary tube 9, it is preferable positioned as close as possible to the spray tip 11 of capillary tube 9 in order to act as efficiently as possible, due regard however being paid to avoiding large disturbances in the electric field between the capillary tube 9 and the inlet plate 17. In practice, a microwave head 21 with 0 Volts applied to it can be introduced to within about 1 cm from the spray tip 11 at 3000 Volts without affecting the quality of the spectra of the mass spectrometer.

While the invention has been illustrated by examples showing a microwave head inside the ionisation chamber, it is of course conceivable to have the microwave head outside the ionisation chamber and to use a waveguide to lead the microwaves to one or more microwave-emitting means inside the ionisation chamber.

While the invention has been illustrated by an example in which the liquid to be analysed comes from a liquid chromatograph, it is possible to apply the device and method of the present invention to any ionisable liquid, irrespective of its source.

Possible Other Claim Formulations

Electrospray device comprising a spray means (11) for producing liquid droplets and a target (19) characterised that it comprises microwave energy emitting means (21) for heating said liquid wherein said microwave-emitting means is positioned between said spray means (11) and said target (19).

Electrospray device in accordance with claim 1 comprising a liquid source (3), an inlet plate (17) with an inlet orifice (19), liquid inlet means such as a capillary tube (9) having an spray tip (11) for emitting liquid from said liquid source (3) wherein said microwave energy emitting means (21) for heating said liquid is positioned between said spray tip (11) and said inlet plate.

What is claimed is:

1. In an electrospray device comprising a liquid source (3) and liquid inlet means (9) having an spray tip (11) for emitting liquid droplets from said liquid source (3) the improvement comprising including microwave energy emitting means (21) for heating said liquid after it has left said spray tip (11).

2. The electrospray device of claim 1 wherein said microwave energy emitting means is a microwave head (21).

3. The electrospray device of claim 1 wherein said microwave energy emitting means (23) is positioned between said spray tip (11) and an inlet orifice (19).

4. The electrospray device of claim 1 which includes a plurality of microwave energy emitting means (21–21").

5. In a method for heating a liquid in an electrospray device wherein said liquid issues from an outlet end (11) of a capillary tube (9) and is directed to an inlet orifice (19) of an inlet plate (17) of a mass analyser (5) the improvement comprising heating said liquid by microwave energy when said liquid is between said spray tip (11) and said mass analyser (5).

6. The method of claim 5 wherein said microwave energy is from a microwave energy emitting means (21) which is positioned to direct microwave energy to droplets after they have left said spray tip (11).

7. The method of claim 5 wherein said microwave energy is from at least two microwave energy emitting means (21–21").

* * * * *